(12) United States Patent
Andersson et al.

(10) Patent No.: US 10,293,964 B2
(45) Date of Patent: May 21, 2019

(54) STERILIZING UNIT COMPRISING A HEATER

(71) Applicant: TETRA LAVAL HOLDINGS & FINANCE S.A., Pully (CH)

(72) Inventors: Jan Andersson, Ystad (SE); Arash Saeidihaghi, Södra Sandby (SE)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 0 days.

(21) Appl. No.: 15/106,579

(22) PCT Filed: Nov. 7, 2014

(86) PCT No.: PCT/EP2014/073989
§ 371 (c)(1),
(2) Date: Jun. 20, 2016

(87) PCT Pub. No.: WO2015/090720
PCT Pub. Date: Jun. 25, 2015

(65) Prior Publication Data
US 2017/0001742 A1    Jan. 5, 2017

(30) Foreign Application Priority Data

Dec. 20, 2013 (SE) ...................... 1351565

(51) Int. Cl.
*B65B 55/06* (2006.01)
*B65B 55/10* (2006.01)
(Continued)

(52) U.S. Cl.
CPC ............... *B65B 55/06* (2013.01); *A61L 2/04* (2013.01); *A61L 2/18* (2013.01); *B65B 55/103* (2013.01);
(Continued)

(58) Field of Classification Search
CPC .......... B65B 55/06; B65B 55/103; A61L 2/18
See application file for complete search history.

(56) References Cited

U.S. PATENT DOCUMENTS 3,158,886 A   12/1964 Grimes
3,383,831 A   5/1968 Goldsmith
(Continued)

FOREIGN PATENT DOCUMENTS

CN   202169427 U   3/2012
DE   41 24 684 A1   1/1993
(Continued)

OTHER PUBLICATIONS

International Search Report (PCT/ISA/210) dated Jan. 22, 2015, by the European Patent Office as the International Searching Authority for International Application No. PCT/EP2014/073989.
(Continued)

*Primary Examiner* — Kevin Joyner
(74) *Attorney, Agent, or Firm* — Buchanan Ingersoll & Rooney PC

(57) ABSTRACT

A sterilizing unit comprising at least one heater is provided, wherein said heater comprises a housing and at least one heating element extending in said housing for heating a flow of air being directed through the housing, and wherein said heating element is formed as a band of an electrically conductive material.

14 Claims, 2 Drawing Sheets

(51) Int. Cl.
  *A61L 2/18* (2006.01)
  *F24H 3/04* (2006.01)
  *H05B 3/40* (2006.01)
  *F24H 9/18* (2006.01)
  *A61L 2/04* (2006.01)
  *B65B 9/00* (2006.01)

(52) U.S. Cl.
  CPC ......... *F24H 3/0405* (2013.01); *F24H 9/1863* (2013.01); *H05B 3/40* (2013.01); *B65B 9/00* (2013.01); *H05B 2203/005* (2013.01)

(56) References Cited

U.S. PATENT DOCUMENTS

| | | | | |
|---|---|---|---|---|
| 3,470,351 | A | | 9/1969 | Fischer |
| 3,651,304 | A | * | 3/1972 | Fedor ................ F24H 3/0405 219/200 |
| 3,691,348 | A | | 9/1972 | Kunz |
| 4,100,395 | A | * | 7/1978 | Ballard ................ H05B 3/08 219/542 |
| 2005/0076612 | A1 | * | 4/2005 | Andersson ............ B65B 55/103 53/167 |
| 2009/0084722 | A1 | | 4/2009 | Atteberry et al. |
| 2015/0334775 | A1 | * | 11/2015 | De Luca ................ A21B 1/22 392/416 |

FOREIGN PATENT DOCUMENTS

| | | |
|---|---|---|
| DE | 20 2013 009 112 U1 | 12/2013 |
| EP | 1 795 448 A1 | 6/2007 |
| GB | 1340539 A | 12/1973 |
| JP | S48-045935 A | 6/1973 |
| JP | S51-007327 B | 3/1976 |
| JP | 2009-517294 A | 4/2009 |
| WO | 2007/063067 A1 | 6/2007 |
| WO | WO 2009/148373 A1 | 12/2009 |

OTHER PUBLICATIONS

Written Opinion (PCT/ISA/237) dated Jan. 22, 2015, by the European Patent Office as the International Searching Authority for International Application No. PCT/EP2014/073989.

Office Action (Notification of Reasons for Refusal) dated Aug. 27, 2018, by the Japanese Patent Office in corresponding Japanese Patent Application No. 2016-541247, and an English Translation of the Office Action. (8 pages).

Office Action in corresponding Japanese Patent Application No. 2016-541247 dated Mar. 12, 2019 (6 pages).

* cited by examiner

STERILIZING UNIT COMPRISING A HEATER

TECHNICAL FIELD

The present invention relates to a sterilizing unit comprising a heater. More particularly, the present invention relates to a heater for increasing the temperature of an air flow in a sterilizing unit for a filling machine.

BACKGROUND

Heaters are currently being used for a vast amount of applications. One such application is during sterilizing of packaging materials in a filling machine being configured to convert a web of packaging material into a series of individual packages enclosing liquid food.

In such application, sterilizing of the packaging material prior to filling may be performed by feeding the packaging material through a bath of hydrogen peroxide. Exposing the packaging material to hydrogen peroxide with subsequent heating will kill all unwanted micro-organisms, since heating will increase the sterilizing effect of the hydrogen peroxide. Heating does not only provide for efficient sterilizing, but also provides an additional effect by drying the packaging material before sealing and filling the individual packages.

For this purpose heaters are normally provided whereby sterile air, or other suitable hygienic gases, is heated before flowing over the surface area of the sterilized packaging material.

In practice, the web of packaging material is running fast through the sterilizing bath whereby it is necessary to have efficient heaters being capable of heating the gas flow to its required temperature in short time. However, should there be a situation when the heaters are needed to be shut off it is desired to provide fast cooling of the heaters, as well as of the packaging material inside the sterilizing unit in order to avoid damage of the packaging material.

Previously this problem has been solved by providing a separate cooling system being configured to spray a mist of cold sterile water onto the packaging material while the heaters are cooling down. Such solution however requires additional components leading to increased complexity and costs. There is thus need for an improved heater which does not damage an adjacent packaging material upon shut-off.

SUMMARY

An object of the invention is to mitigate the above problem. This object is achieved by the technique defined in the appended independent claims; preferred embodiments being defined in the related dependent claims.

According to one aspect, a sterilizing unit comprising at least one heater is provided. The heater comprises a housing and at least one heating element extending in said housing for heating a flow of air being directed through the housing, wherein the heating element is formed as a band of an electrically conductive material. A band should in this context be interpreted broadly as a structure having a high surface area compared to its mass. By such configuration the heating element will cool rapidly in case of a sudden shut down thus preventing damage of components being arranged adjacent to the heater, such as packaging material inside a sterilizing unit.

The band may e.g. have a thickness between 0.01 and 0.05 mm, and a width between 2 and 10 cm.

In some embodiment, the band has a uniform surface area.

In other embodiments the band is formed as a wire netting. The wire netting may be formed by metal wire having a thickness between 0.02 and 2 mm, and the wires may be spaced apart by a distance of 0.01-0.05 mm. In one embodiment the wire netting is corrugated. A corrugated wire netting is advantageous by the fact that such netting will not bend transversal to its longitudinal direction, i.e. in the direction of the air flow. Such bending would affect the air flow significantly. Hence, in case the band has a uniform surface area it is also possible to corrugate the band in order to benefit from the same advantages as in the case of a corrugated wire netting.

The heating element may extend from one lateral side of the housing to the opposite side of the housing in a meandering manner such that the heating element extends back and forth in the housing.

The heating element may be spring biased for applying a tension force to the heating element. For example, the heating element may be connected to the housing by means of a plurality of rollers, and wherein each one of at least some of the rollers is attached to the housing by means of a spring.

The heater may further comprise at least one guiding plate through which the heating element is guided such that the angle of the heating element relative the housing changes.

The heater may comprise a plurality of heating elements being stacked in the same direction as air is allowed to flow through the heater.

The sterilizing unit may further comprise a fan being arranged adjacent to said heater for providing a flow of air through the heater.

BRIEF DESCRIPTION OF DRAWINGS

Embodiments of the present invention will be described in the following, reference being made to the appended drawings, wherein.

DETAILED DESCRIPTION

Figure 1:
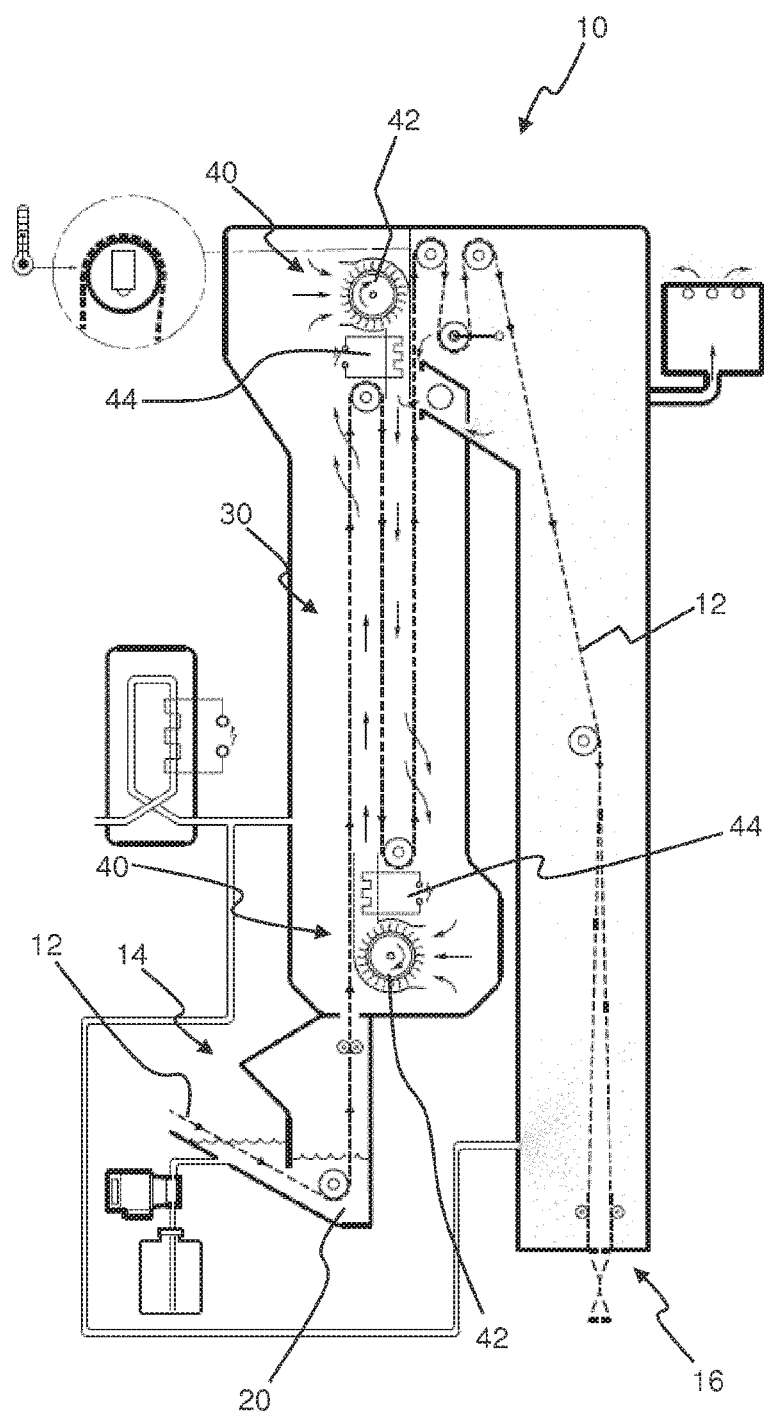
FIG. 1 is a cross-sectional view of a sterilizing unit having two heaters according to an embodiment.

Starting with FIG. 1, a sterilizing unit 10 is shown. The sterilizing unit 10 is arranged in a filling machine for converting a web of packaging material 12 to individual liquid food packages.

The sterilizing unit 10 has an inlet 14 for allowing the web of packaging material 12 to enter the sterilizing unit 10, and an outlet 16 for allowing the web 12 to be further guided to a forming and filling section (not shown).

Once entering the sterilizing unit 10, the web 12 will be transported through a bath 20 of sterilizing liquid, e.g. comprising hydrogen peroxide which is a very suitable liquid for sterilizing different kinds of materials, including a carton-based material having one or several polymeric layers laminated thereupon.

In order to ensure that the web 12 is sufficiently sterilized when entering the subsequent filling station a heating section 30 is provided. The heating section 30 forms a path for the web 12, and provides a flow of hot air or other gases for drying the web 12 when travelling along the path. The heating section 30 has two heating units 40, wherein each heating unit 40 has a fan 42 and an associated heater 44. In the shown example the heating units 40 are arranged vertically, such that an upper heating unit 40 is arranged to provide a flow of hot air downwards, while a lower heating unit 40 is arranged to provide a flow of hot air upwards. The path for the web 12 is preferably arranged such that the upper heating unit 40 will provide a flow of hot air to one side of the web 12, while the lower heating unit 40 will simultaneously provide a flow of hot air to the opposite side of the web 12.

Now turning to FIG. 2 a heater 44 will be described. The heater 44 has a housing 441 forming a support for a heating element 442. Generally, the housing 441 has four sidewalls leaving the upper and lower ends open for allowing air to flow through the heater 44. The heating element 442 is formed by an electrically conductive material, such as stainless steel, in the form of a band having a very high surface area compared to its mass. For example, in one embodiment, a band is used being approximately 0.03 mm thick and having a width of 2-10 cm, such as approximately 5 cm. In a further embodiment, the heating element 442 is formed by an electrically conductive material in the form of a wire netting, wherein the width of each wire is between 0.02 and 0.2 mm, preferably around 0.1 mm, and wherein the distance between each wire is below 1 mm, preferably around 0.25 mm.

The heating element 442 is supported at one lateral end of the housing 441 and extends along the length of the housing 441 to the opposite end, where it is guided to turn approximately 180° thus returning to the lateral end of the starting point. As can be seen in FIG. 2, the heating element 442 is guided several times from one lateral end to the other, such that the total length of the heating element corresponds to a multiple of the length of the housing 441.

For allowing the heating element 442 to turn at the lateral ends several rollers 443 are provided, wherein at least some of the rollers 443 being attached to the housing 441 by means of springs 444. The springs 444 are chosen such that they pull the rollers 443 towards the lateral end to which it is supported such that the rollers 443 will apply a tensioning force to the heating element 442 at each position of a roller 443. The rollers 443 are preferably made of an electrically insulating material, such as ceramic.

In one embodiment, each roller 443 is attached to the housing 441 by means of a spring. In other embodiments, only some of the rollers 443 are attached to the housing 441 by means of springs 444. In one embodiment, all rollers 443 of one side of the housing 441 are attached to the housing by means of springs 444, while the rollers 443 on the opposite side of the housing 441 are rigidly attached to the housing 441.

The starting point and the end point for the heating element 442 are preferably arranged at the same lateral end such that an electrical power source 445 may be connected easily without the need for excessive cables. Hence, when the electrical power source 445 is activated a current will flow through the heating element 442 whereby the intrinsic resistance of the heating element 442 will generate heat.

The number of turns for the heating element 442, i.e. the number of rollers 443 on each lateral side of the housing 441, may be chosen depending on the particular application. For example, the number of rollers 443 may be 8 and 9, respectively for the different lateral sides of the housing 441.

Figure 2:
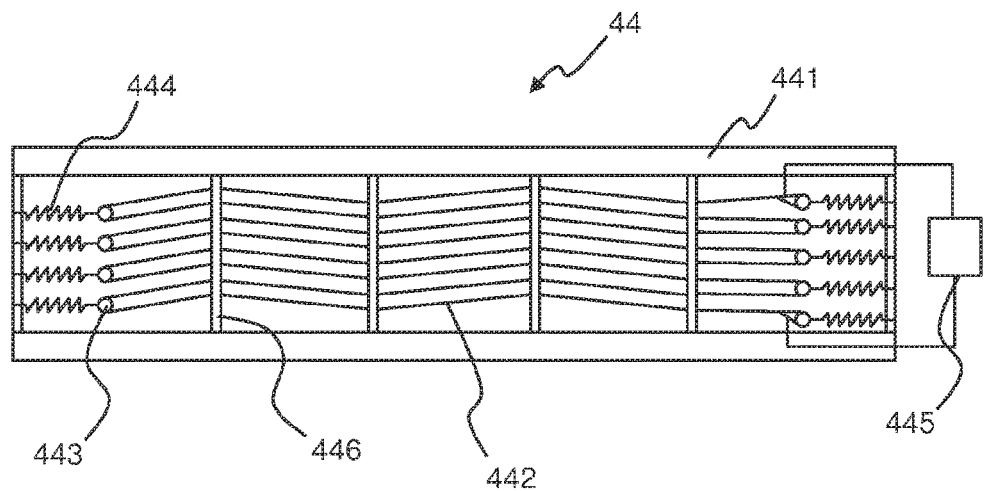
FIG. 2 is a top view of a heater according to an embodiment.

As can be further seen in FIG. 2 a number of guiding plates 446 are distributed along the length of the housing 441. Each guiding plate 446 may be formed by ceramic rods being supported by lateral supports. The diameter of each rod may e.g. be 3 mm. Hence, the guide plates 446 comprise recesses through which the heating element 442 may be extending. Each recess is arranged with an offset relative the rollers 443 such that the heating element 442, running from a roller 443, must change its angle once passing the guiding plate 446. The heating element 442 will thus be subject to support points along its length, each support point being caused by the interaction between the heating element 442 and a guiding plate 446. The main reason for providing the guiding plates 446 is to decrease the free length of the heating element 442. For the sterilizing unit 10 shown in FIG. 1, the adjacent fan 42 will cause a significant air flow through the heater 44 which will cause the heating element 442 to oscillate. By reducing the free length the oscillations will decrease, thus reducing noise and the risk for temporary contact between different portions of the heating element 442.

As previously mentioned, each roller 443 is preferably made of an electrically insulating material, such as ceramic, for isolating the housing from the electrically conducting heating element 442. The rollers 443 may also be provided as metal rods having ceramic bushings. Hence, the springs 444 may be attached to the rollers 443 from above and/or below, thus preventing the springs 443 from contacting the heating element 442.

Figure 3:
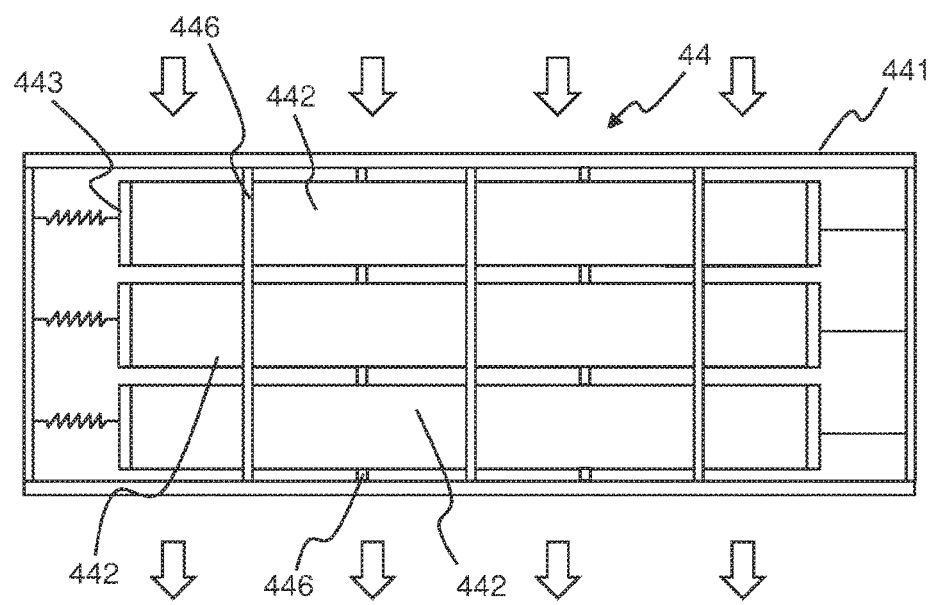
FIG. 3 is a cross-sectional view of a heater according to an embodiment.

Now turning to FIG. 3 a cross-sectional view of the heater 44 shows three heating elements 442 arranged vertically. Air is flowing in the direction of the arrows, thus indicating the provision of open ends of the housing 441.

Each heating element 442 is supported in the housing 441 in accordance with the description relating to FIG. 2, i.e. by means of springs 444 and associated guiding rollers 443. However, as can be seen in FIG. 2 only the rollers 443 of one lateral side are attached by means of springs 444, whereby the rollers 443 of the opposite lateral side are rigidly attached to the housing 441. The exact number of heating elements 442 may depend on the application, however it may be desirable to decrease the width of the heating elements 442 in order to increase the robustness of the heating elements 442. Accordingly, the number of heating elements 442 may be increased in order to still provide sufficient heating of the air flow.

Although the above description has been made mostly with reference to a heater for drying a packaging material web, it should be readily understood that the general principle of the heater is applicable for various different technical fields in which rapid cooling is desired.

Further, the invention has mainly been described with reference to a few embodiments. However, as is readily understood by a person skilled in the art, other embodiments than the ones disclosed above are equally possible within the scope of the invention, as defined by the appended claims.

The invention claimed is:

1. A sterilizing unit comprising at least one heater, wherein said heater comprises a housing and at least one heating element extending in said housing for heating a flow of air being directed through the housing, and wherein said heating element is formed as a band of an electrically conductive material, said band being formed as a wire netting, wherein said wire netting is corrugated in a longitudinal direction in which the heating element extends and perpendicular to a direction of the flow of air through the housing, wherein the heating element is connected to the housing by a plurality of rollers, and wherein at least more than one of the rollers are attached to the housing by a spring which is electrically isolated from the heating element.

2. The sterilizing unit according to claim 1, wherein said band has a thickness between 0.01 and 0.05 mm, and a width between 2 and 10 cm.

3. The sterilizing unit according to claim 1, wherein said band has a uniform surface area.

4. The sterilizing unit according to claim 1, wherein the wire netting is formed by metal wire having a thickness between 0.02 and 2 mm, and wherein the wires are spaced apart by a distance of 0.01-0.05 mm.

5. The sterilizing unit according to claim 1, wherein the heating element extends from one lateral side of the housing to the opposite side of the housing in a meandering manner.

6. The sterilizing unit according to claim 1, further comprising at least one guiding plate through which the heating element is guided such that the angle of the heating element relative the housing changes.

7. The sterilizing unit according to claim 1, comprising a plurality of heating elements being stacked in the same direction as air is allowed to flow through the heater.

8. The sterilizing unit according to claim 1, further comprising a fan being arranged adjacent to said heater for providing a flow of air through the heater.

9. A sterilizing unit for sterilizing a packaging material web which is subsequently converted into individual liquid food packages, the sterilizing unit comprising:
   an inlet through which the packaging material web is introduced into the sterilizing unit;
   a sterilizing solution holder for holding a bath of sterilizing solution through which the packaging material web is fed as the packaging material web moves in a direction of travel through the sterilizing unit;
   a heater positioned downstream of the sterilizing solution holder relative to the direction of travel of the packaging material web through the sterilizing unit;
   the heater comprising a heating element positioned in a housing to heat a flow of air directed through the housing, the heating element comprising a band of an electrically conductive material, the band of the electrically conductive material being a single length of the electrically conductive material that extends from one end of the housing to an opposite end of the housing, and from the opposite end of the housing to the one end of the housing, said band being formed as a wire netting, wherein said wire netting is corrugated in a longitudinal direction in which the heating element extends and perpendicular to a direction of the flow of air through the housing, wherein the heating element is connected to the housing by a plurality of rollers, and wherein at least more than one of the rollers are attached to the housing by a spring which is electrically isolated from the heating element.

10. The sterilizing unit according to claim 9, wherein the band has a uniform surface along a length of the band.

11. The sterilizing unit according to claim 9, further comprising a fan positioned relative to the heater such that the heater is positioned between the fan and the packaging material web when the packaging material web is conveyed through the sterilizing unit.

12. The sterilizing unit according to claim 9, further comprising at least one guiding plate through which the heating element passes such that the angle of the heating element relative the housing changes.

13. The sterilizing unit according to claim 9, wherein the heater comprises a plurality of stacked heating elements, each of the heating elements comprising one of the bands of electrically conductive material that is a single length of the electrically conductive material extending from the one end of the housing to the opposite end of the housing, and from the opposite end of the housing to the one end of the housing.

14. The sterilizing unit according to claim 9, wherein the wire netting is formed by metal wire having a thickness between 0.02 and 2 mm, and wherein the wires are spaced apart by a distance of 0.01-0.05 mm.

* * * * *